US00PP35887P2

(12) United States Plant Patent
Wilson

(10) Patent No.: US PP35,887 P2
(45) Date of Patent: Jun. 25, 2024

(54) ***ECHINACEA* PLANT NAMED 'DWGBO20'**

(50) Latin Name: *Echinacea purpurea*
Varietal Denomination: DWGBO20

(71) Applicant: David Wilson, Bridgeton, NJ (US)

(72) Inventor: David Wilson, Bridgeton, NJ (US)

(73) Assignee: Overdevest Nurseries, Bridgeton, NJ (US)

( * ) Notice: Subject to any disclaimer, the term of this patent is extended or adjusted under 35 U.S.C. 154(b) by 0 days.

(21) Appl. No.: 18/244,939

(22) Filed: Sep. 12, 2023

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
See application file for complete search history.

*Primary Examiner* — Susan McCormick Ewoldt
(74) *Attorney, Agent, or Firm* — Cassandra Bright

(57) ABSTRACT

A new and distinct cultivar of *Echinacea purpurea* plant named 'DWGBO20' is disclosed, characterized by large, fully double chrysanthemum-like inflorescences composed of ray florets arranged consistently in a dome. Plants are bushy and sturdy with an upright habit. Free and continuous flowering begins in June and continues through September. *Echinacea* is a popular genus, typically used as container plants or landscape plants.

2 Drawing Sheets

Latin name of the genus and species: *Echinacea purpurea.*

Variety denomination: 'DWGBO20'.

BACKGROUND OF THE INVENTION

The new variety, *Echinacea* 'DWGBO20', is the product of a planned breeding program by the inventor. The crossing resulting in the new variety was made during July of 2020 at a commercial nursery in Bridgeton, NJ. The seed parent is an unnamed, unpatented proprietary variety of *Echinacea purpurea*. The pollen parent is a different unnamed, unpatented proprietary variety of *Echinacea purpurea*. The discovery was made during July of 2021, in Bridgeton, NJ, at the same commercial nursery.

Asexual reproduction of the new variety 'DWGBO20' was first performed Bridgeton, NJ, at the same commercial nursery, by divisions in April of 2023. Plants from this reproduction of *Echinacea* 'DWGBO20' have shown that the unique features of this variety are stable and reproduced true to type.

SUMMARY OF THE INVENTION

The variety 'DWGBO20' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DWGBO20'. These characteristics in combination distinguish 'DWGBO20' as a new and distinct *Echinacea* variety:

1. Large, fully double (Chrysanthemum-like) inflorescences.
2. Free and continuous flowering.

3. Multiple broad petals (ray florets) arranged & displayed consistently in a dome.
4. Bushy, sturdy, upright habit.

PARENTAL COMPARISON

Plants of the new variety 'DWGBO20' are similar to plants of the seed parent in most horticultural characteristics. However, plants of the new variety 'DWGBO20' differ in the following:

1. Inflorescences of the new variety are fully double; inflorescences of the seed parent are semi-double.
2. Plants of the new variety are bushier and less open than plants of the seed parent.

Plants of the new variety 'DWGBO20' are similar to plants of the pollen parent in most horticultural characteristics. However, plants of the new variety 'DWGBO20' differ in the following:

1. Inflorescences of the new variety are fully double; inflorescences of the pollen parent are semi-double.
2. Plants of the new variety are shorter than plants of the pollen parent.
3. Plants of the new variety are more floriferous than plants of the pollen parent.

COMMERCIAL COMPARISON

The new variety 'DWGBO20' can be compared to the commercial variety *Echinacea* 'Lovely Lolly' (unpatented). Plants of the new variety 'DWGBO20' differ in the following:

1. Plants of the new variety are about 80 cm in height, while plants of this comparator are about 50 cm in height.
2. Inflorescence shape of the new variety is a flattened dome; inflorescence shape of this comparator is spherical.
3. Inflorescences of the new variety are lighter and brighter in color.

4. Inflorescences of the new variety are wider than inflorescences of this comparator.

The new variety 'DWGBO20' can be compared to the patented *Echinacea* 'Razzmatazz', U.S. Plant Pat. No. 13,894. Plants of the new variety 'DWGBO20' differ in the following:

1. Inflorescence shape of the new variety is a flattened dome; inflorescence shape of this comparator is anemone.
2. Plants of the new variety produce more inflorescences than plants of this comparator.

BRIEF DESCRIPTION OF THE PHOTOGRAPHS

The photographs were taken using conventional techniques and equipment. While the colors in these photographs may display variances of color as compared to the living variety, due to LRV (light reflectance value), they are as accurate as possible using conventional photographic techniques. Colors in the photographs may appear to differ slightly from the color values cited in the botanical description, which accurately describe the colors of new *Echinacea* 'DWGBO20'. Plants were grown in Bridgeton, NJ.

DETAILED BOTANICAL DESCRIPTION

Figure 1:
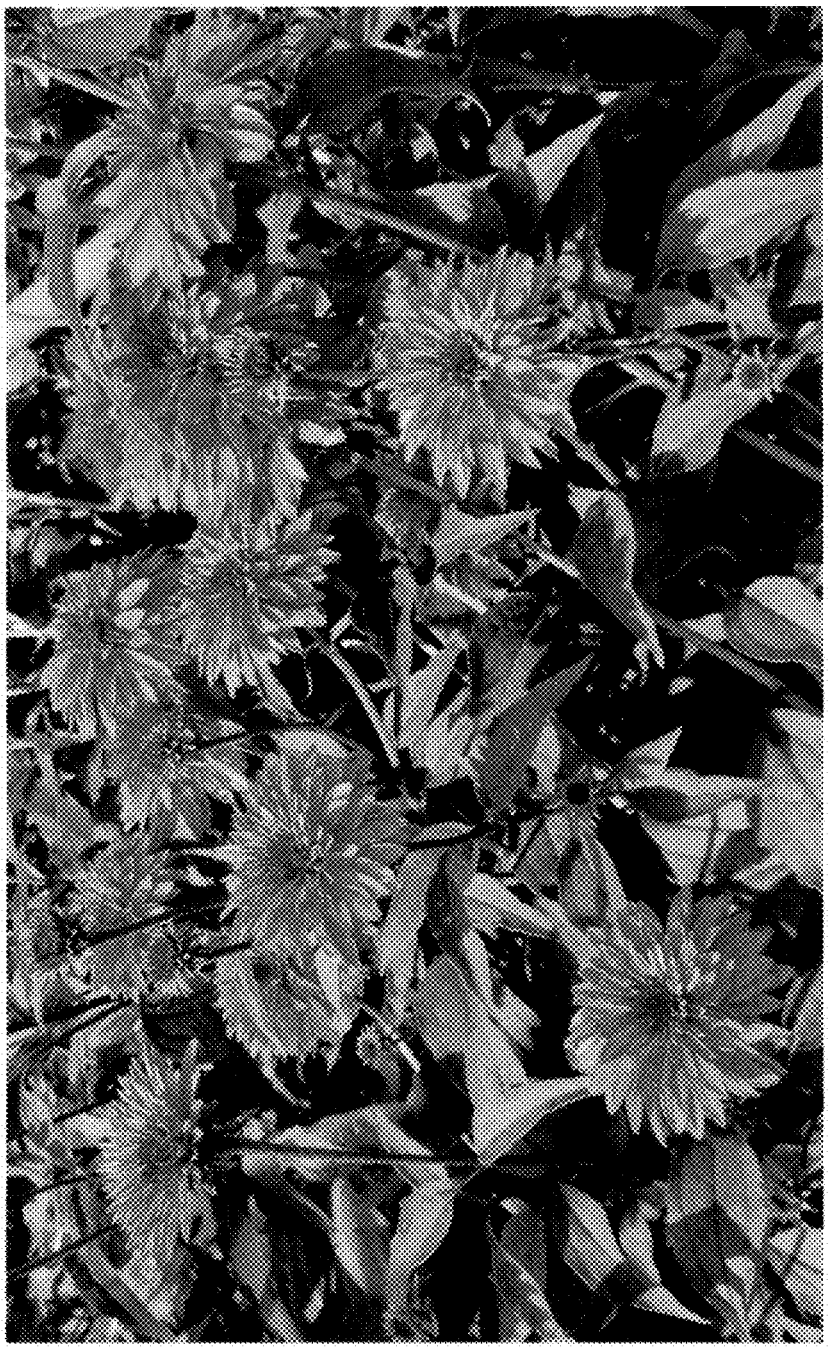
FIG. 1 illustrates in full color a plant of *Echinacea* 'DWGBO20' grown in the ground at approximately 1 year old.
Figure 2:
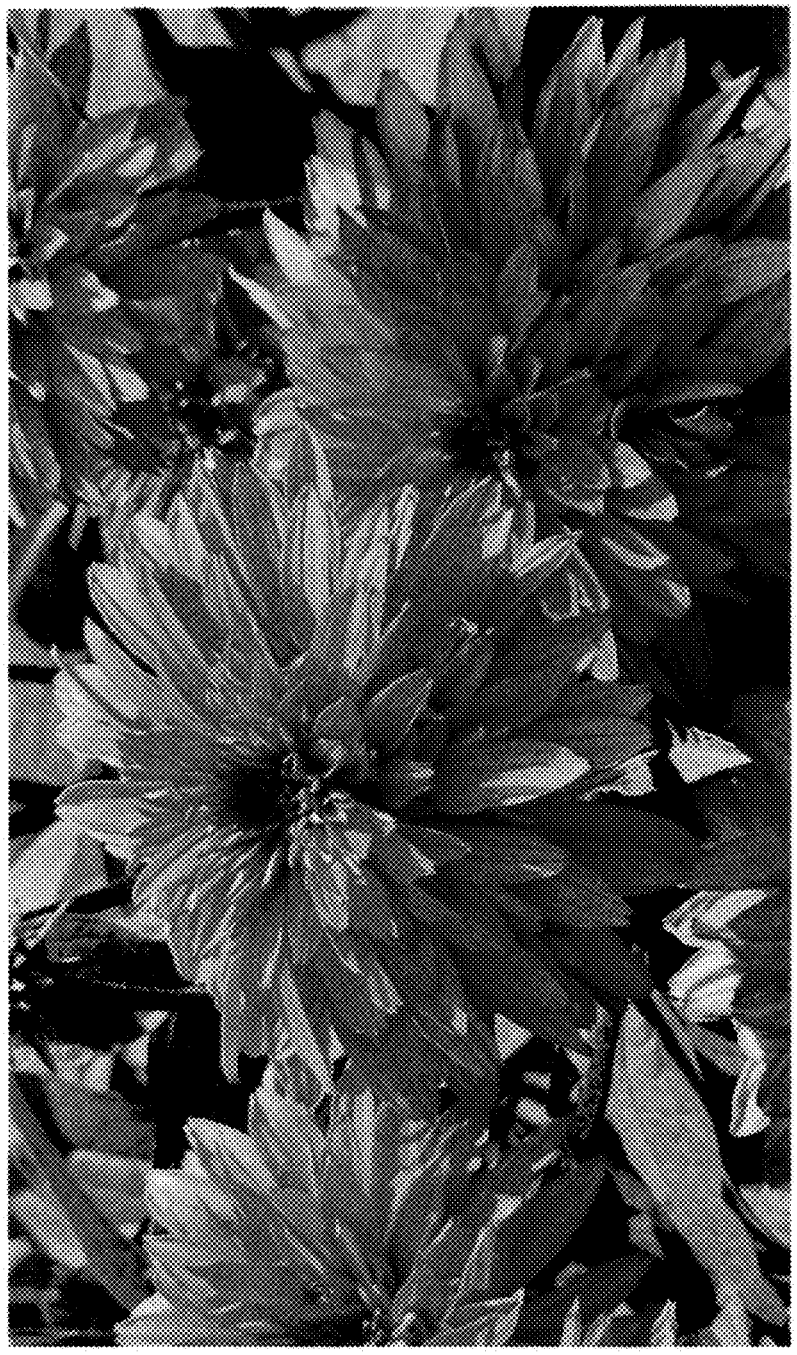
FIG. 2 illustrates in full color a close-up view of the inflorescences of *Echinacea* 'DWGBO20' at maturity.

In the following description, color references are made to The Royal Horticultural Society Colour Chart, 2007, except where general terms of ordinary dictionary significance are used. The following observations and measurements describe 'DWGBO20' plants grown outdoors in Bridgeton, NJ. Measurements and numerical values represent averages of typical plant types.

Botanical classification: *Echinacea purpurea* 'DWGBO20'.

PROPAGATION

Time to rooting: 10 days at approximately 19° C.
Time to produce a rooted cutting: Approximately 40 days.
Root description: Fibrous. Young roots white, older roots creamy white-brown. Colors not accurately measured with R.H.S. chart.

PLANT

Growth habit: Hardy, upright, herbaceous perennial.
Blooming period: Naturally blooming June to September (Bridgeton, NJ).
Height: Approximately 80 cm.
Plant spread: Approximately 80 cm.
Growth rate: Vigorous.
Branching characteristics: Well Branched and bushy.
Length of lateral branches: Approximately 80 cm.
Diameter of lateral branches: Approximately 1 cm (at base).
Quantity of lateral branches: Approximately 16.
Texture of lateral branches: Hirsute.
Color of lateral branches: Near RHS Yellow-Green 144B.
Internode length: Average 7 cm.
Number of leaves per lateral branch: Approximately 32.
Age of plant described: Approximately 4 months from a division.

FOLIAGE

Leaf:
- *Arrangement*.—Alternate, simple.
- *Average length*.—Smallest apical leaves approximately 3.5 cm. Largest basal leaves approximately 16 cm.
- *Average width*.—Smallest apical leaves approximately 1 cm. Largest basal leaves approximately 7.5 cm.
- *Shape of blade*.—Broad lanceolate.
- *Apex*.—Acuminate.
- *Base*.—Attenuate.
- *Attachment*.—Upper leaves sessile; basal leaves stalked.
- *Margin*.—Entire.
- *Texture of top surface*.—Moderately hispid.
- *Texture of bottom surface*.—Moderately hispid.
- *Leaf internode length*.—Approximately 13 cm.
- *Color*.—Young foliage upper side: Near Yellow-Green 144A. Young foliage under side: Near Green 137B. Mature foliage upper side: Near Green 137A. Mature foliage under side: Near Green 137B.
- *Venation*.—Type: Pinnate. Venation color upper side: Near RHS Yellow-Green 144C. Venation color under side: Near RHS Yellow-Green 144D.

Petiole: Basal leaves only.
- *Length*.—Approximately 15 cm.
- *Diameter*.—Approximately 0.3 cm.
- *Texture*.—Glabrous.

FLOWER

Blooming period: Naturally blooming June to September (Bridgeton, NJ).

Bud:
- *Bud shape*.—Globular.
- *Bud length*.—Approximately 1 cm.
- *Bud diameter*.—Approximately 1 cm.
- *Bud color*.—Near Greyed-Orange 166C flushed Greyed-Red 180D.

Inflorescence:
- *Form*.—Composite, fully double.

Flower:
- *Diameter of entire flower*.—Approximately 10 cm to 13 cm.
- *Depth of flower*.—Approximately 7 cm to 8 cm.
- *Disc diameter*.—Approximately 5 cm.
- *Receptacle shape*.—Hemispherical.
- *Receptacle height*.—Average 3.5 cm.
- *Receptacle diameter*.—Average 4 cm.
- *Quantity of inflorescences per lateral stem*.—7 to 10.
- *Quantity of open inflorescences and buds per plant*.—Average 58.
- *Longevity*.—Approximately 2 weeks.
- *Rate of opening*.—1 to 10 days from bud to fully opened flower.
- *Persistent or self-cleaning*.—Persistent.

Ray florets:
- *Arrangement*.—Whirled, arising all over disc area.
- *Aspect/orientation*.—Flat and slightly recurving/reflexing.
- *Shape*.—Narrowly oblanceolate.
- *Number of ray florets*.—Average range 155 to 200.

*Length*.—Approximately 5 cm (outer), 3.5 cms (middle), 2 cm to 3 cms (center).
*Width*.—Approximately 1 cm. outer; 0.5 cm in center.
*Apex shape*.—Incised with two acute tips.
*Base*.—Attenuate.
*Margin*.—Entire.
*Texture*.—Smooth.
*Color*.—Upper surface at first opening: Near RHS Red-Purple 59D lightly flushed N57B and Greyed-Purple 185B. Upper surface at maturity: Near RHS Red-Purple 64C lightly flushed N57B; base 64B. Upper surface at fading: Near RHS Red-Purple 64C flushed 64D. Under surface at first opening: Near RHS Red-Purple 59D. Under surface at maturity: Near RHS Red-Purple 64C. Under surface at fading: RHS Red-Purple 64D.

Disc florets:
*Number of disc florets*.—Approximately 200.
*Arrangement*.—Spirally arranged in center of each inflorescence.
*Length*.—Approximately 0.1 cm.
*Width*.—Approximately 2.5 mm.
*Shape*.—Tubular.
*Margin*.—Entire.
*Apex*.—Five acute tips.
*Base*.—Fused into tube.
*Texture*.—Glabrous, glossy.
*Receptacle spines*.—Number of spines per disc floret: 1. Spine shape: Cylindrical with conical tips. Spine apex: Acute. Spine texture: Glabrous, glossy.
*Color*.—At first opening: Near RHS Yellow Green 144B. At maturity: Near RHS Yellow Green N144D.

Fragrance: Faint.

Phyllaries/involucral bracts:
*Arrangement*.—Three whorls.
*Number*.—Approximately 50.
*Length*.—Approximately 1 cm.
*Width*.—Approximately 0.25 cm.
*Shape*.—Narrowly ovate to lanceolate.
*Apex*.—Acute.
*Base*.—Truncate.
*Margin*.—Entire, hispid.
*Texture*.—Glabrous.
*Color*.—Inside color: Near RHS Yellow Green 144C. Outside color: Near RHS Yellow Green 144C.

Peduncle:
*Length*.—Average range 25 to 40 to cm.
*Width*.—Average 0.5 cm.
*Texture*.—Moderately hispid.
*Color*.—Near RHS Yellow-Green 153B.

REPRODUCTIVE ORGANS

Androecium:
*Stamens per disc floret*.—4.
*Filament length*.—Approximately 0.2 cm.
*Filament color*.—Near RHS Yellow-Green 145C.
*Anther shape*.—Oblong.
*Anther length*.—About 0.2 cm.
*Anther color*.—Near RHS Brown 200A.
*Pollen amount*.—Abundant.
*Pollen color*.—Near RHS Yellow-Orange 15B.

Gynoecium:
*Pistil length*.—Approximately 0.6 cm.
*Stigma shape*.—Decurrent.
*Stigma color*.—Near RHS Yellow-Green 151D.
*Style length*.—About 0.5 cm.
*Style color*.—Near RHS Yellow-Green 145C.
*Ovary color*.—Near RHS Yellow-Green 145D.

OTHER CHARACTERISTICS

Fruits and seeds: Fertile, some seed set. About 3 to 5 seeds per flower head. Seeds achene, about 3 mm to 5 mm long and about 2 mm wide. Colored near Grey-Brown 199A.

Temperature tolerance: USDA Zones 3 through 8.

Disease/pest resistance: Neither resistance nor susceptibility to normal diseases and pests of *Echinacea* has been observed.

Drought tolerance: Good drought tolerance, established plants can tolerate infrequent summer watering.

What is claimed is:

1. A new and distinct cultivar of *Echinacea* plant named 'DWGBO20' as herein illustrated and described.

* * * * *